(12) United States Patent
Ehring et al.

(10) Patent No.: US 10,185,088 B2
(45) Date of Patent: Jan. 22, 2019

(54) OPTICAL FIBER ARRANGEMENT FOR A SYSTEM FOR MEASURING THE LIGHT ABSORPTION OR DETERMINING THE CONCENTRATION OF A SUBSTANCE

(71) Applicant: GE HEALTHCARE BIO-SCIENCES AB, Uppsala (SE)

(72) Inventors: Hanno Ehring, Uppsala (SE); Siavash Yazdanfar, Niskayuna, NY (US); Mikael Anders Hornqvist, Uppsala (SE); Zhangyi Zhong, Niskayuna, NY (US); Ying Mao, Niskayuna, NY (US)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 0 days.

(21) Appl. No.: 15/533,670

(22) PCT Filed: Dec. 18, 2015

(86) PCT No.: PCT/EP2015/080417
§ 371 (c)(1),
(2) Date: Jun. 7, 2017

(87) PCT Pub. No.: WO2016/097256
PCT Pub. Date: Jun. 23, 2016

(65) Prior Publication Data
US 2017/0322080 A1    Nov. 9, 2017

Related U.S. Application Data

(60) Provisional application No. 62/093,481, filed on Dec. 18, 2014.

(51) Int. Cl.
*G02B 6/14* (2006.01)
*G02B 6/36* (2006.01)
(Continued)

(52) U.S. Cl.
CPC .............. *G02B 6/14* (2013.01); *G01J 3/0218* (2013.01); *G01J 3/42* (2013.01); *G01N 30/74* (2013.01);
(Continued)

(58) Field of Classification Search
None
See application file for complete search history.

(56) References Cited

U.S. PATENT DOCUMENTS 4,735,484 A * 4/1988 Fesler ................. G02F 1/0134
                                                         359/287
5,244,636 A * 9/1993 Walt ................... G01N 21/6456
                                                         250/227.23
(Continued)

FOREIGN PATENT DOCUMENTS

DE         3411272 A1 * 10/1985
DE    102007028081 B3    11/2008
(Continued)

OTHER PUBLICATIONS

B. Culshaw et al. Evanescent wave methane detection using optical fibres. Electronics Letters, 28:24:2232-2234, Nov. 19, 1992.*
(Continued)

*Primary Examiner* — Michael Stahl
(74) *Attorney, Agent, or Firm* — Eversheds Sutherland (US) LLP

(57) ABSTRACT

Disclosed is an optical fiber arrangement for inducing coupling among propagation modes of light, said arrangement comprising a multimode optical fiber (30) having an input end (32) for receiving light and an output end (31) for emitting light, with a coupling inducing section (33) extending from said input end to said output end, and a holder (80) on which the optical fiber is arranged, wherein said multimode optical fiber has a non-circular cross section. Dis-
(Continued)

closed also is a system for measuring the absorption or determining the concentration of a substance, said system comprising at least one optical fiber arrangement.

20 Claims, 3 Drawing Sheets

(51) Int. Cl.
G01J 3/02 (2006.01)
G01J 3/42 (2006.01)
G01N 30/74 (2006.01)
G02B 6/028 (2006.01)
G01N 30/02 (2006.01)
G02B 6/00 (2006.01)

(52) U.S. Cl.
CPC ..... *G02B 6/3628* (2013.01); *G01N 2030/027* (2013.01); *G02B 6/00* (2013.01); *G02B 6/0288* (2013.01)

(56) References Cited

U.S. PATENT DOCUMENTS

| 6,157,763 | A  | * | 12/2000 | Grubb ............... G02B 6/03622 372/6 |
| 6,917,746 | B2 | * | 7/2005 | Simmons ................. G02B 6/43 385/137 |
| 6,963,062 | B2 | * | 11/2005 | Cyr ........................ G01N 21/31 250/227.25 |
| 9,719,917 | B2 |   | 8/2017 | Frojdh et al. |
| 2001/0019652 | A1 | * | 9/2001 | DiGiovanni ...... C03B 37/01228 385/123 |
| 2004/0037496 | A1 | * | 2/2004 | Pierce .................. G02B 6/4206 385/28 |
| 2009/0109698 | A1 | * | 4/2009 | Koyata ................ G02B 6/0008 362/553 |
| 2010/0290738 | A1 | * | 11/2010 | Yan ......................... G02B 6/14 385/28 |
| 2012/0147362 | A1 |   | 6/2012 | Crowther et al. |
| 2013/0293874 | A1 | * | 11/2013 | Goldstein ............ G01M 11/088 356/73.1 |
| 2014/0212089 | A1 | * | 7/2014 | Dimmick ................. G02B 6/24 385/27 |
| 2014/0321798 | A1 | * | 10/2014 | Chen ..................... C03C 25/107 385/12 |

FOREIGN PATENT DOCUMENTS

| GB | 1420458 | 1/1976 |
| JP | S-60178409 A | 9/1985 |

OTHER PUBLICATIONS

T.B. Colin et al. The effect of mode distribution on evanescent field intensity: applications in optical fiber sensors. Applied Spectroscopy, 45:8:1291-1295, Aug. 1991.*

Newport Corporation, FM-1 Mode Scrambler Instruction Manual, Aug. 2000. retrieved from https://www.newport.com/medias/sys_master/images/images/hbc/h09/8974578384926/IN-11851-FM-1.pdf.*

PCT International Search Report and Written Opinion for PCT Application No. PCT/EP2015/080417 dated Apr. 20, 2016 (9 pages).

Chinese Office Action for CN Application No. 2015800691182 dated Jun. 1, 2018 (14 pages, English translation).

* cited by examiner

OPTICAL FIBER ARRANGEMENT FOR A SYSTEM FOR MEASURING THE LIGHT ABSORPTION OR DETERMINING THE CONCENTRATION OF A SUBSTANCE

CROSS REFERENCE TO RELATED APPLICATIONS

This application claims the priority benefit of PCT/EP2015/080417 filed on Dec. 18, 2015 which claims priority benefit of U.S. Provisional Patent Application No. 62/093,481 filed Dec. 18, 2014. The entire contents of which are hereby incorporated by reference herein.

FIELD OF THE INVENTION

The present invention relates to an optical fiber arrangement for inducing coupling among propagation modes of light. The invention also relates to a system for measuring the light absorption or determining the concentration of a substance for example a substance suspended in a solution, said system comprising an optical fiber arrangement, for example in a liquid chromatography spectrophotometer.

BACKGROUND OF THE INVENTION

Optical detection methods are frequently employed in analytical instruments for sensitive detection of chemical compounds, such as biomolecules. Optical detection is particularly well suited for analytical techniques where the absorption or the concentration of a substance are measured or determined, such as liquid chromatography or filtering systems, which are important tools in biotechnological, biomedical and biochemical research as well as in the pharmaceutical, cosmetics, energy, food and environmental industries.

Typically, the optical systems associated with liquid chromatography use a series of lenses and mirrors to collect and propagate light from a light source to a flow cell, through which a fluid containing a sample is allowed to flow. Light not absorbed after passing through this cell strikes a light detector containing one or more photosensitive elements and is subsequently analyzed to provide information regarding the sample.

Often, and in order to achieve satisfactory results of the analyses, optical fibers are used for propagating light within the system. This has the advantages of minimizing the use of optical elements such as collimating lenses and reflectors, as well as providing a flexible transfer of lights and a minimal loss of intensity, even over extended distances.

The light source can be a xenon lamp, for instance, that emits flashes of light at certain intervals. Due to factors such as fluctuation of intensity, baseline drift and temperature drift, it is often necessary to arrange the optical fiber in a series of bends and loops to allow for a coupling of propagation modes that serves to provide a smooth output of light, regardless of fluctuations of the input from the light source. Such an arrangement of the optical fiber can be denoted as a mode coupling fiber arrangement. Especially for applications where a beam splitter is used to split the light into two portions, in order to provide a stable reference portion that is not transmitted to the flow cell, it is important that the output from the optical fiber is as uniform as possible in order to achieve satisfactory results.

Methods for mode coupling within the field of liquid chromatography are known in the art, for instance through loops, microbends or notches. Examples of such solutions can be found in U.S. Pat. No. 6,963,062 (Eksigent Tech, LLC), U.S. Pat. No. 7,945,130 (General Photonics Corp.) or U.S. Pat. No. 4,676,594 (American Telephone & Telegraph).

The mode coupling or mode mixing arrangement commonly used has the disadvantages of being bulky and requiring a relatively long optical fiber to allow for a sufficient coupling of optical modes.

Through the loops and bends, transmission losses also occur, especially in the deep UV region below 250 nm. If the bend radius is kept large, the losses are smaller but the mode coupling ability is decreased, requiring an even longer fiber in order to achieve an output of sufficient quality.

The problems associated with liquid chromatography as described above are also applicable to other systems for measuring the absorption or determining the concentration of a substance, where a stable reference value is required. Such systems comprise filtering systems, cell harvesting systems, clarification systems, formulation systems and similar systems for production of biopharmaceuticals, among others.

There is therefore a need for an optical fiber arrangement with improved mode coupling suitable for such systems without the disadvantages described above.

SUMMARY OF THE INVENTION

The object of the invention is to achieve an improved mode coupling in an optical fiber arrangement suitable for use in systems for measuring the light absorbance or determining the concentration of a substance. This is achieved through an optical fiber arrangement for inducing coupling among propagation modes of light according to the appended independent claim 1. Thereby, the mode coupling is performed in an efficient manner, achieving uniform output light of high quality.

According to an aspect of the invention, the coupling inducing section of the optical fiber is arranged essentially in a plane on said holder. Thereby, the entire optical fiber arrangement can be made smaller and more stable, avoiding any movements of the coupling inducing section due to insufficient fixation, and the losses associated therewith.

According to a further aspect of the invention, the coupling inducing section of the optical fiber comprises a plurality of regions and each region is fixated in relation to said holder. Thereby, losses and drift that occur through position changes of the optical fiber, through temperature drift or due to external forces applied to the optical fiber can be minimized.

According to another aspect of the invention, the coupling inducing section is arranged along a path in said holder, said path comprising open bends such that no region of the coupling inducing section is arranged to overlap any other region. Thereby, any losses occurring through the movement or abutting of one part of the optical fiber on another can be minimized, and the fixation of the entire coupling inducing section is facilitated.

According to a further aspect of the invention, the holder has a surface and a plurality of holding pins propagating from said surface, said holding pins having a first diameter near said surface and a second diameter at a distance from said surface, wherein the first diameter is smaller than the second diameter. Thereby, the pins interact with the optical fiber to hold it in relation to the surface and by the first diameter being smaller than the second diameter the optical fiber is prevented from moving.

According to yet another aspect of the invention, at least one of the holding pins is movably arranged on the surface of the holder. Thereby, the fixation of the optical fiber can be further improved and tolerances in the length of the fiber can be compensated to achieve a secure fastening and prevent movements of the optical fiber.

One aspect of the invention includes a liquid chromatography spectrophotometer including any one of the aspects above, and arranged to accept the output flow from a chromatographic separation column.

Further advantages and benefits of the invention will become readily apparent to the person skilled in the art in view of the detailed description below.

BRIEF DESCRIPTION OF THE FIGURES

The invention will now be described in more detail with reference to the appended drawings, wherein.

DETAILED DESCRIPTION OF THE INVENTION

The optical fiber arrangement according to a preferred embodiment of the invention is suitable for use in a system for measuring the absorption or determining the concentration or a substance selected from the group comprising proteins, peptides, nucleic acids or cells within a solution. One example of such systems is a liquid chromatography system, and a typical system of this kind is disclosed by FIG. 1 and used below to illustrate the invention.

Figure 1:
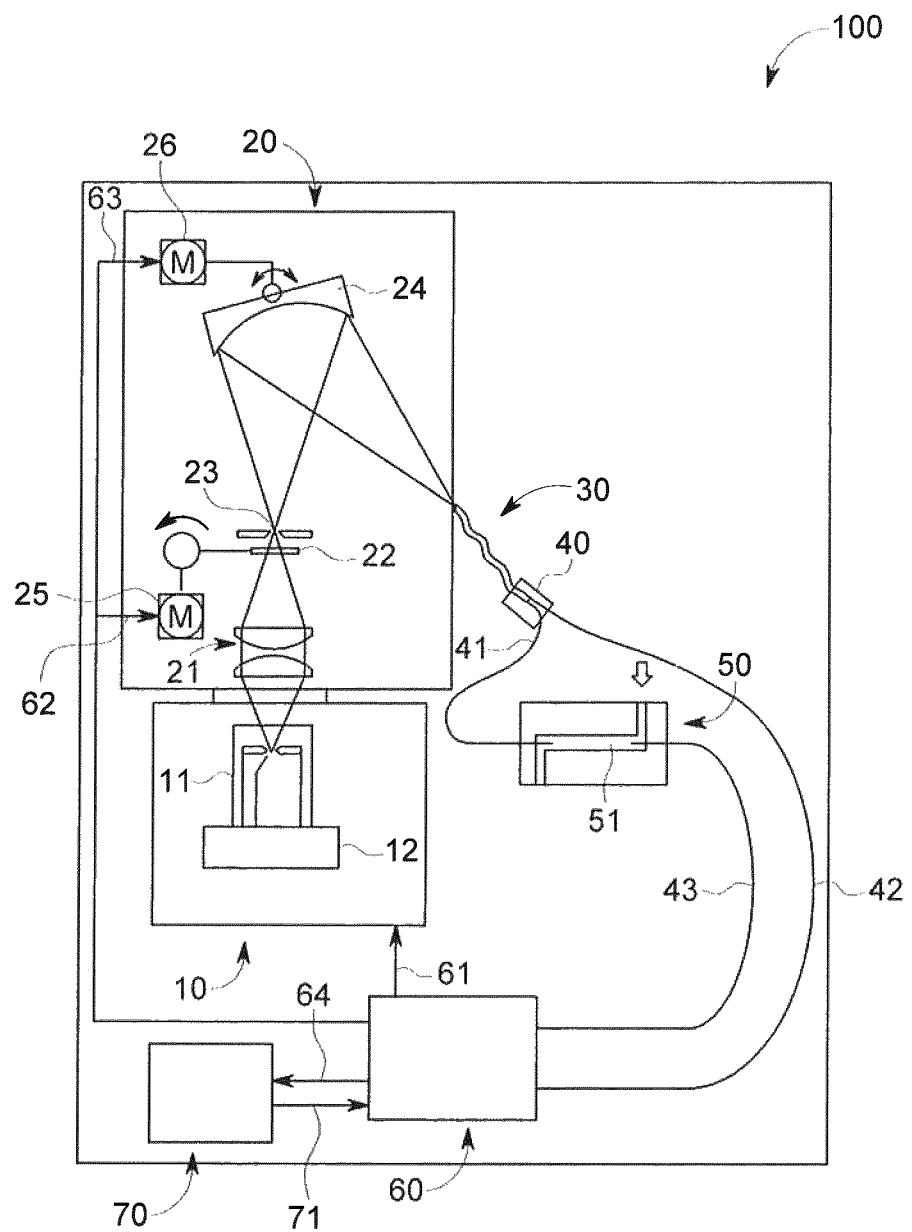
FIG. 1 is a schematic diagram of a typical liquid chromatography system with an optical fiber arrangement according to the invention.

Thus, FIG. 1 shows a schematic diagram of a typical liquid chromatography system 100, including a spectrophotometer with a light source unit 10 comprising a light source 11 and a lamp trigger 12 that is arranged to control the light source 11 to emit flashes of light at predetermined intervals. The light source 11 can be a xenon lamp with a frequency of 100 Hz, but alternatively other suitable light sources can be used. Light emitted by the light source 11 propagates to a monochromator 20 and passes a condenser 21 to focus the light towards an entrance slit 23 before reaching an aberration corrected holographic grating 24 that reflects the light and that projects it onto an input end 32 of a first optical fiber 30. Before reaching the entrance slit 23, the light is also transmitted to a high pass filter 22 that removes light of wavelengths below a set cutoff frequency, for instance 360 nm, if the visible region of light is to be used. Furthermore, the filter 22 is controlled by a first stepper motor 25 that can remove the filter 22 from the path of light if light in the UV range is to be used by the system instead of visible light.

The light emitted in each flash from the light source 11 generally differs from each other flash, due to irregularities in the intensity of the lamp used or due to small movements of the light source 11 in relation to the monochromator 20 or to temperature drift during operation of the liquid chromatography system 100. However, in order to achieve satisfactory results from measurements performed in the system, the modes of light are mixed by the first optical fiber 30 so that output light that is emitted from the first optical fiber 30 has a uniform mode distribution regardless of these factors.

Figure 2:
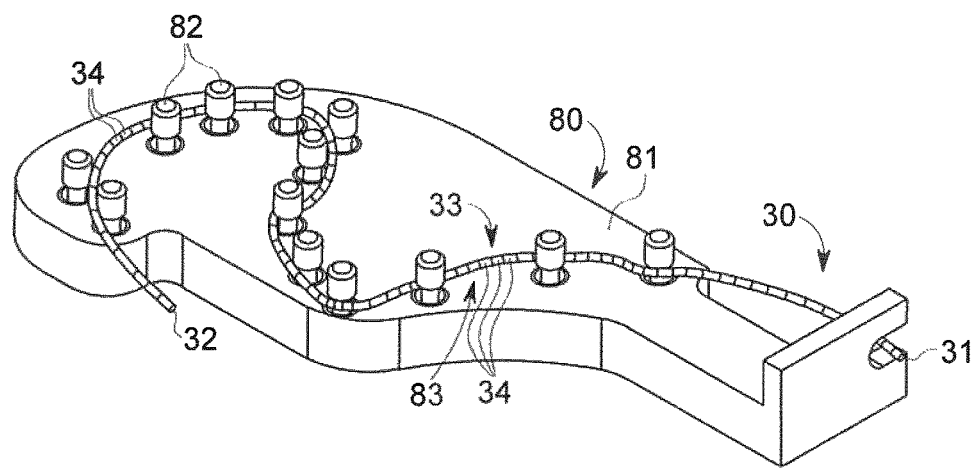
FIG. 2 is a perspective view of a holder with an optical fiber of an optical fiber arrangement according to the invention.

The first optical fiber 30 is therefore a multimode optical fiber that is arranged to receive the light projected on the input end 32 and allow it to propagate along a coupling inducing section 33 to an output end 31 from which it is emitted to a beam splitter 40. The coupling inducing section 33 extends from the input end 32 to the output end 31 and serves to induce coupling among propagation modes of the light received at the input end 32, i.e. to mix the modes of light, in order to achieve a smooth output light that has a uniform distribution. The coupling inducing section 33 can be said to comprise a plurality of regions 34 (see FIG. 2).

Thus, the light emitted from the output end 31 of the first optical fiber 30 is projected onto a beam splitter 40 and split into a first portion of light that is transmitted in a second optical fiber 42 to a control unit 60 in order to provide a reference value, and a second portion of light that is transmitted in a third optical fiber 41 to a flow cell unit 50, arranged to accept sample fluid flow from a chromatographic separation column (illustrated schematically by the thick arrow), and allowed to irradiate a flow cell 51 through which a sample fluid flows. From the flow cell 51, the light is transmitted in a fourth optical fiber 43 to the control unit 60 to serve as a sample value. The control unit 60 comprises optical detectors suitable for detecting light from the second and fourth optical fibers 42, 43, and by comparing the sample value and the reference value, the control unit 60 is arranged to determine properties of the sample in the flow cell 51, such as the presence and quantity of a particular molecule.

The control unit 60 is also arranged to control the operation of the liquid chromatography system 100 by a plurality of control signals. Thus, a first control signal 61 controls the lamp trigger 12 and thereby the operation of the light source 11, a second control signal 62 controls the first stepper motor 25 and thereby the position of the filter 22, and a third control signal 63 controls the second stepper motor 26 and thereby the operation of the aberration corrected holographic grating 24 that projects the light onto the first optical fiber 30. Furthermore, the control unit 60 provides system output signals 64 such as signals regarding the measurements of the properties of the sample in the flow cell 51, among others.

An external control unit 70, such as a PC, is arranged to receive the system output signals 64 and can for instance save them, use them for calculations and present data to a user. The external control unit 70 is also arranged to control the operation of the control unit 60 by a series of system input signals 71, for instance regarding the frequency of the light source 11, the position of the filter 22, how the light should be projected onto the first optical fiber 30 by the grating 24, or which wavelength range is to be detected by the optical detectors. These input control signals 71 can be determined by a user.

Figure 3:
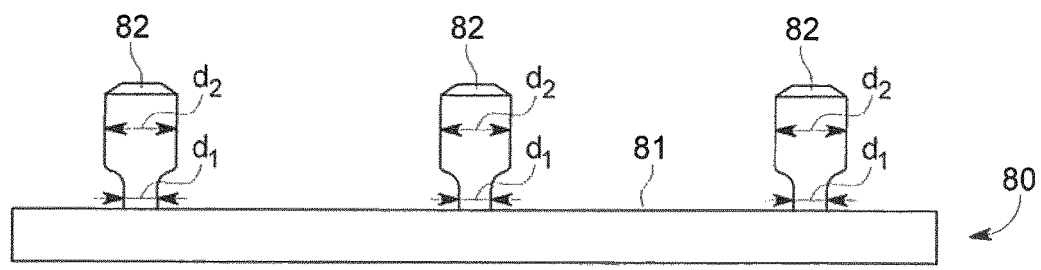
FIG. 3 is a planar view from the side of a holder of FIG. 2.

The invention will now be described in detail and with reference to the liquid chromatography system 100 described above and to FIGS. 2-3.

According to a preferred embodiment of the invention, the first optical fiber 30 is arranged in a holder 80 and held by fastening means 82 along a path 83 comprising a series of open bends from the input end 32 to the output end 31. Thanks to the bends, the propagation modes are coupled so that after the light has been subjected to total internal reflection many times along the coupling inducing section 33, a thorough mode mixing has been achieved.

Furthermore, the first optical fiber 30 has a non-circular cross section, preferably octagonal but alternatively hexagonal, rectangular or decagonal, for instance. This is greatly advantageous in allowing for an efficient coupling of propagation modes, i.e. mixing of the light propagated through the optical fiber. Therefore, the coupling can be performed with an increased efficiency compared to multimode optical fibers having a circular cross-section, and a thorough mixing producing a uniform output of light from each flash of the light source 11 can be achieved with a shorter length of coupling inducing section 33 and thereby a shorter total fiber length than would be possible according to the prior art using circular fibers.

Figure 4A:
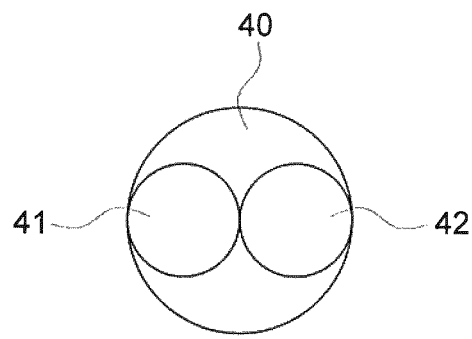
FIG. 4a is a cross-sectional view of two optical fibers with circular cross section at a beam splitter.
Figure 4B:
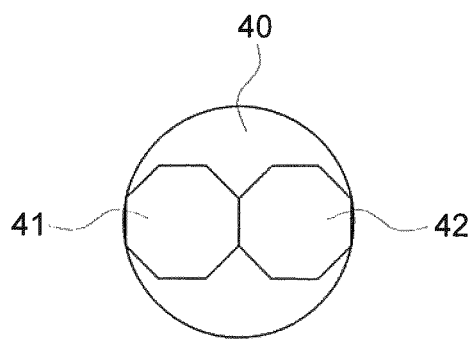
FIG. 4b is a cross-sectional view of two optical fibers with octagonal cross section at a beam splitter.

The second optical fiber 42 and the third optical fiber 41, that are arranged at the beam splitter 40 to receive one portion each of the light emitting from the first optical fiber 30, preferably also have a non-circular cross section. In some arrangements, having non-circular second 42 and third 41 optical fibers is advantageous in minimizing the losses at the beam splitter, where said second and third optical fibers 42, 41 can be arranged with an input end of each optical fiber 42, 41 side by side to receive the light being projected onto the beam splitter 40. When using optical fibers with a circular cross-section and arranging them side by side, a significant portion of the light projected onto input ends of the fibers is lost, as is shown by FIG. 4a, disclosing two circular input ends of the second and third optical fibers 42, 41 at a beam splitter 40, and by FIG. 4b, disclosing two octagonal input ends of the second and third optical fibers 42, 41 at a beam splitter 40. It will be appreciated that the beam splitter's cross section may not be the circular cross section shown in FIGS. 4a and 4b for example the cross section may match the cross section of the first optical fiber 30, and therefore may be octagonal etc. in cross section.

In many prior art systems, the multimode optical fiber is arranged in bends and loops projecting in three dimensions from the input end to the output end. Often, the loops are not supported by the holder, except at a base of the loop. In this preferred embodiment of the present invention, however, the path along which the coupling inducing section 33 is held comprises only open bends arranged in such a way that no region 34 of the coupling inducing section 33 overlaps any other region 34. Thus, the coupling inducing section 33 is not arranged in a loop and does not project in three dimensions, but rather extends essentially in a plane on a surface 81 of the holder 80 from the input end 32 to the output end 31. This has the advantage that a smaller and more stable holder 80 can be used and that every region 34 of the coupling inducing section 33, i.e. every point along the coupling inducing section 33, can be securely fastened and fixated in relation to the surface 81 of the holder 80. Thanks to this secure fastening, intensity losses and drift in the first optical fiber 30 can be kept at a minimum and a high quality of the light emitting from the output end 31 can be achieved. If desired, the input end 32 and the output end 31 can also be fastened on the holder 80, so that every part of the first optical fiber 30 is fixated.

The fastening means 82 serve to secure the first optical fiber 30 on the holder 80, and can comprise a fastening device in the form of a groove along the path 83, a plurality of hooks or clips, an adhesive, a lid pressed onto the optical fiber, or any other suitable kind of fastening means. In this preferred embodiment, the fastening means 82 are a plurality of holding pins 82 that project from the surface 81 at desired places along the path 83. The holding pins 82 extend essentially orthogonally from the surface 81 (see FIG. 3) and have a first diameter $d_1$ close to the surface and a second diameter $d_2$ at a distance from the surface 81, such that the first diameter $d_1$ is smaller than the second diameter $d_2$.

Thus, the holding pins 82 are thinner at a base connected to the surface 81 and widen towards a top of the holding pins 82. Thanks to this shape, the first optical fiber 30 can be securely held along the path without requiring other fastening devices, and small movements such as slippage along the holding pins 82 away from the surface 81 can be avoided.

In this embodiment, the holding pins 82 are all similar in shape and size to each other, but alternatively one or more holding pins 82 can differ as desired in order to provide a secure fastening of the first optical fiber. Also, one or more of the pins 82 can be arranged to be movable, e.g. slidable, in relation to the surface 81 to facilitate a fixation of the first optical fiber 30 and compensate for small tolerances in the length of the optical fiber 30. The laterally slidable pins can also be used to modify or gradually adjust the mode coupling efficiency.

When mounting the first optical fiber 30, the coupling inducing section is put into place along the path, held by the holding pins, and the input end 32 and the output end 31 are fastened as desired, such that every region 34 along the first optical fiber 30 is fixated in relation to the holder 80 and the surface 81 of said holder 80. If any of the holding pins 82 is movably arranged, the mounting can be performed by putting the first optical fiber 30 into place along the path 83 and then sliding the holding pins 82 that are movable into a desired place such that the first optical fiber is fixated. The holding pins can then be secured in relation to the holder 80, for instance by a screw or other fastening device that prevents further movements of the holding pins 82.

To achieve a secure fastening of the optical fiber 30 to the holder 80 is also advantageous during manufacture of the system, since any internal tensions in the optical fiber 30 created during mounting are more easily relaxed if the optical fiber is fixated, thereby decreasing the initial baseline drift.

The invention is not to be seen as limited by the embodiments described above, but can be varied within the scope of the appended claims, as will be readily understood by the person skilled in the art. For instance, the optical fiber arrangement according to the invention can be used in a variety of different liquid chromatography systems and can also be used in different technical applications where a coupling of propagations modes in an optical fiber are beneficial and a stable reference signal is required, such as filtering systems, cell harvesting systems, clarification systems, formulation systems, or similar systems for production of biopharmaceuticals, as well as within other technical fields.

The invention claimed is:

1. A system for measuring light absorption or determining a concentration of a substance, the system comprising:
    an optical fiber arrangement for inducing coupling among propagation modes of light, the optical fiber arrangement comprising:
        a multimode optical fiber comprising an input end for receiving light, an output end for emitting light, and a coupling inducing section extending from the input end to the output end, wherein the multimode optical fiber has a non-circular cross section,
        a holder, and
        fastening means arranged to secure the multimode optical fiber in the holder;
    a second optical fiber comprising an input end, wherein the second optical fiber has a non-circular cross section;
    a third optical fiber comprising an input end, wherein the third optical fiber has a non-circular cross section; and a beam splitter arranged at the output end of the multimode optical fiber, wherein the beam splitter is arranged to project light on the input end of the second optical fiber and the input end of the third optical fiber.

2. The system according to claim 1, wherein the coupling inducing section is arranged essentially in a single plane at the holder.

3. The system according to claim 1, wherein the coupling inducing section comprises a plurality of regions, and wherein each region is fixed in relation to the holder.

4. The system according to claim 1, wherein the coupling inducing section is arranged along a path in the holder, and wherein the path comprises open bends such that no region of the coupling inducing section is arranged to overlap any other region of the coupling inducing section.

5. The system according to claim 1, wherein the holder has a surface, wherein the fastening means comprises a plurality of holding pins propagating from the surface, wherein each of the holding pins has a first diameter adjacent to the surface and a second diameter at a distance from the surface, and wherein the first diameter is smaller than the second diameter.

6. The system according to claim 5, wherein the coupling inducing section is held along the surface of the holder by the holding pins.

7. The system according to claim 6, wherein at least one of the holding pins is movably arranged on the surface of the holder.

8. The system according to claim 5, wherein the holding pins extend orthogonally from the surface.

9. The system according to claim 1, wherein the input end and the output end of the multimode optical fiber are fastened on the holder.

10. The system according to claim 1, wherein the multimode optical fiber has an octagonal cross section.

11. The system according to claim 1, wherein the multimode optical fiber has a hexagonal cross section, a rectangular cross section, or a decagonal cross section.

12. The system according to claim 1, wherein the second optical fiber and the third optical fiber each have an octagonal cross section.

13. The system according to claim 1, further comprising a control unit, wherein the second optical fiber is arranged to transmit a first portion of light emitted from the beam splitter to the control unit.

14. The system according to claim 13, further comprising a flow cell unit, wherein the third optical fiber is arranged to transmit a second portion of light emitted from the beam splitter to the flow cell unit.

15. The system according to claim 14, wherein the flow cell unit is arranged to accept a sample fluid flow from a chromatographic separation column, and wherein the second portion of light irradiates a flow cell of the flow cell unit.

16. The system according to claim 15, further comprising a fourth optical fiber arranged to receive light from the flow cell and transmit light to the control unit.

17. The system according to claim 1, further comprising:
a light source; and
a monochromator arranged to receive light emitted by the light source and direct light to the input end of the multimode optical fiber.

18. The system according to claim 17, wherein the monochromator comprises an aberration corrected holographic grating arranged to reflect light emitted by the light source and project light to the input end of the multimode optical fiber.

19. The system according to claim 18, wherein the monochromator further comprises a condenser arranged to focus light emitted by the light source.

20. The system according to claim 19, wherein the monochromator further comprises a high pass filter arranged to receive light from the condenser and remove light of wavelengths below a cutoff frequency.

* * * * *